United States Patent [19]
Lee

[11] Patent Number: 6,007,502
[45] Date of Patent: Dec. 28, 1999

[54] ION FACIAL MASSAGE SYSTEM

[75] Inventor: Heung-soon Lee, Seoul, Rep. of Korea

[73] Assignee: Worldra Co., Ltd., Rep. of Korea

[21] Appl. No.: 09/046,940

[22] Filed: Mar. 23, 1998

[51] Int. Cl.[6] ............................... A61N 1/30; A61N 1/44;
A45D 40/24; A45D 40/18
[52] U.S. Cl. ............................ 601/17; 604/20; 132/286;
132/314; 607/115; 607/150; 607/50; 601/21;
601/138
[58] Field of Search ................................. 604/20; 607/50,
607/72, 75, 150, 115, 148, 145, 3, 149,
153; 132/286, 294, 303, 271; 601/15, 17,
18, 20, 21, 46, 48, 136, 137, 138, 72, 80

[56] References Cited

U.S. PATENT DOCUMENTS

| | | |
|---|---|---|
| 3,809,977 | 5/1974 | Balamuth et al. . |
| 4,010,742 | 3/1977 | Kim . |
| 4,655,232 | 4/1987 | Ficke ..................................... 132/79 A |
| 4,944,302 | 7/1990 | Hernandez et al. . |
| 5,010,896 | 4/1991 | Westbrook . |
| 5,086,788 | 2/1992 | Castel et al. . |
| 5,655,553 | 8/1997 | Giese et al. .............................. 132/303 |
| 5,931,859 | 8/1999 | Burke ..................................... 604/20 X |

FOREIGN PATENT DOCUMENTS 95003726 2/1995 WIPO ..................................... 132/314

*Primary Examiner*—Danton D. DeMille
*Attorney, Agent, or Firm*—R. Neil Sudol; Henry D. Coleman

[57] ABSTRACT

The present invention relates to an ion facial massage system including a case having a plurality of grooves formed on a top surface thereof for being inserted with cosmetic containers respectively, a plurality of switches provided at one side of the case for being pressed to carry out respective stages of massage, an ion lamp provided at one side of the case for displaying an ion-generating state, and a battery lamp provided at one side of the case for displaying a battery-consuming state, an ion-generating member for electrically generating ions in respective stages of massage in response to pressing of the switches, and an ion-effusion member to be detachably fitted in an inserting groove formed on the case for effusing the electrically generated ions, wherein not only effete materials are removed but also the nutrition components of the cosmetics and collagen are absorbed deep into the inner skin beyond the barrier zone by means of ions, thereby strengthening the elasticity of the cellula tissue of the inner skin and the generation function of natural hydration factors, and promoting fission functions of new cells.

4 Claims, 5 Drawing Sheets

FIG.5
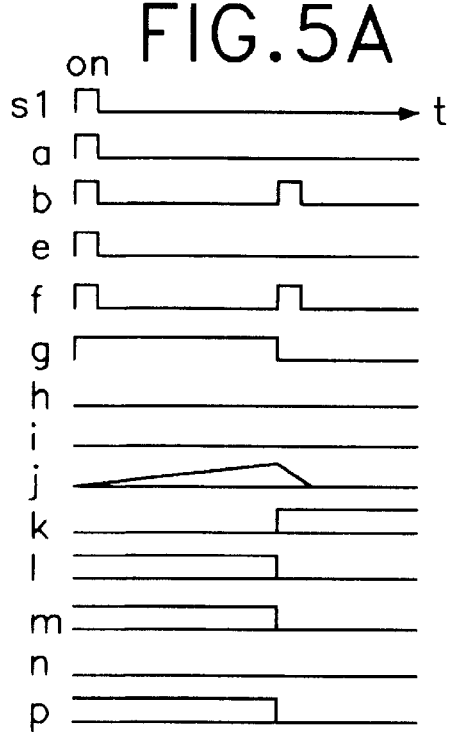
FIG.5A
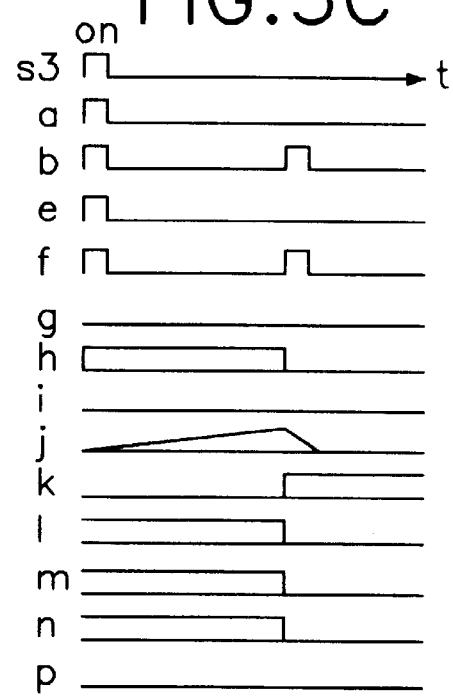
FIG.5C
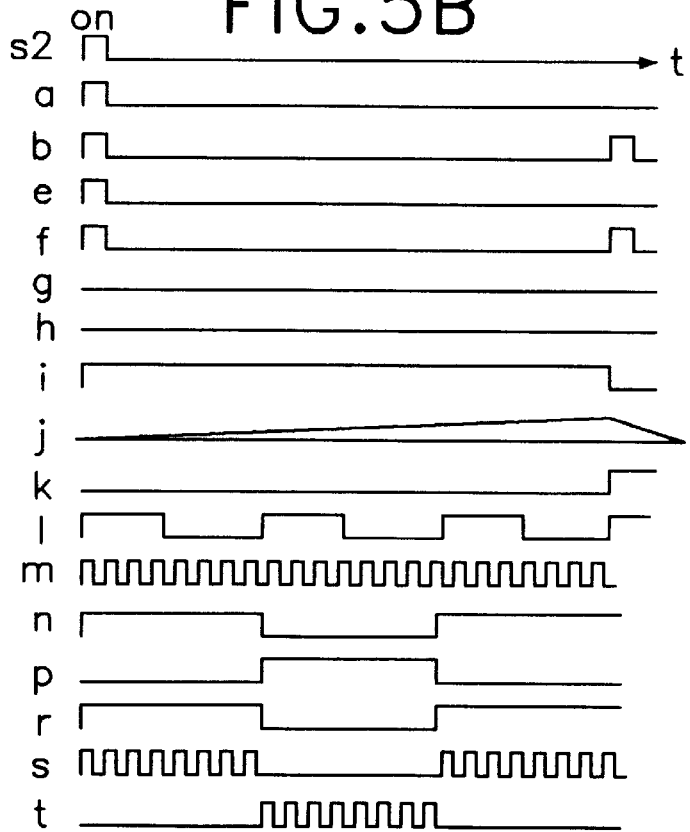
FIG.5B

ION FACIAL MASSAGE SYSTEM

TECHNICAL FIELD

The present invention relates to an ion facial massage system, and particularly to, an improved ion facial massage system by which facial skin may be changed transparent and soft by absorbing bio substances deep into inner skin even beyond a barrier zone by means of positive ions of the skin and negative ions generated through three stages of massage.

BACKGROUND ART

Generally, human skin is composed of an outer skin layer, an inner skin layer, and a hypoderm skin layer, and the outer skin layer is composed of keratinocyte layer, a transparent cell layer, a granule-cell layer, a prickle-cell layer and a basal cell layer, wherein a barrier zone like a strong fortification is present between the transparent cell layer and the granule-cell layer.

Therefore, regeneration of skin depends on the barrier zone, that is, whether or not nutrition substances permeate this protective layer and reach to the inner skin. However, the nutrition substances cannot permeate the barrier zone and be soaked into the inner skin, and only the keratinocyte layer is supplied with moisture except nutrition components.

In order to solve this problem, Liposome has been suggested and widely known for skin regeneration effect. However, the Liposome is proved not to permeate the barrier zone. According to papers published by American Academic Skin Institute in U.S.A., cosmetics should reach to the inner skin beyond the barrier zone to regenerate the skin.

Liposome can not reach to the inner skin, and supply moisture components to the keratinocyte layer.

Further, in case of mercury, hormone, and vitamin A,D and E, even though they can permeate the barrier zone, they have no particular good effect to improve the facial skin. Especially, it is well known that the mercury or the hormone may cause serious ill side effects.

SUMMARY OF THE INVENTION

Accordingly, the present invention is derived to resolve the above disadvantages of conventional cosmetics and it is an object of the present invention to provide an ion facial massage system in which positive and negative ions having strong resolvent components are generated to extract effete materials out of the inner skin, by means of the positive and negative ions.

It is another object of the present invention to provide an ion facial massage system in which the generated positive and negative ions pass through a barrier zone crossing each other to supply nutrition components to the inner skin, and especially, the positive ions make it possible for bio components such as collagen to be absorbed deep into the inner skin, thereby making the facial skin young end elastic.

To achieve the above object, the present invention is directed to an ion facial massage system that includes a case having a plurality of grooves formed on a top surface thereof for being inserted with cosmetic containers respectively, a plurality of switches provided at one side of the case for being pressed to carry out respective stages of massage, an ion lamp provided at one side of the case for displaying an ion-generating state, and a battery lamp provided at one side of the case for displaying a battery consuming state, an ion-generating member for electrically generating ions in respective stages of massage in response to pressing of the switches, and an ion-effusion member to be detachably fitted in an inserting groove formed on the case for effusing the electrically generated ions, wherein not only effete materials are removed but also the nutrition components of the cosmetics and collagen are absorbed deep into the inner skin passing through the barrier zone by means of the generated and effused ions, thereby strengthening the elasticity of the cellula tissue of the inner skin and the generation function of natural hydration factors, and promoting fission functions of new cells.

In order to achieve the object of the present invention, the ion facial massage procedure includes the steps of deep cleansing for extracting effet materials, being effectual for oily skin having acnes and motes, toning and vitalizing for strengthen skin elacitiy by contracting skin pores and improving blood circulation, being effectual for removing skin discoloration of age and blotch, and supplying nutrient components to deep inner skin for regenerating new skin cells, being effectual for wrinkles and acne scars.

BRIEF DESCRIPTION OF THE DRAWINGS

The present invention will become more fully understood from the detailed description given hereinafter and the accompanying drawing which are given by way of illustration only, and thus are not limitative of the present invention, and wherein:

FIGS. 5A to 5C are views respectively showing wave forms of input/output signals in the circuit of FIG. 4, according to the present invention.

DISCLOSURE OF THE INVENTION

An ion facial massage system according to the present invention will now be described in detail with reference to the annexed drawings.

Figure 1:
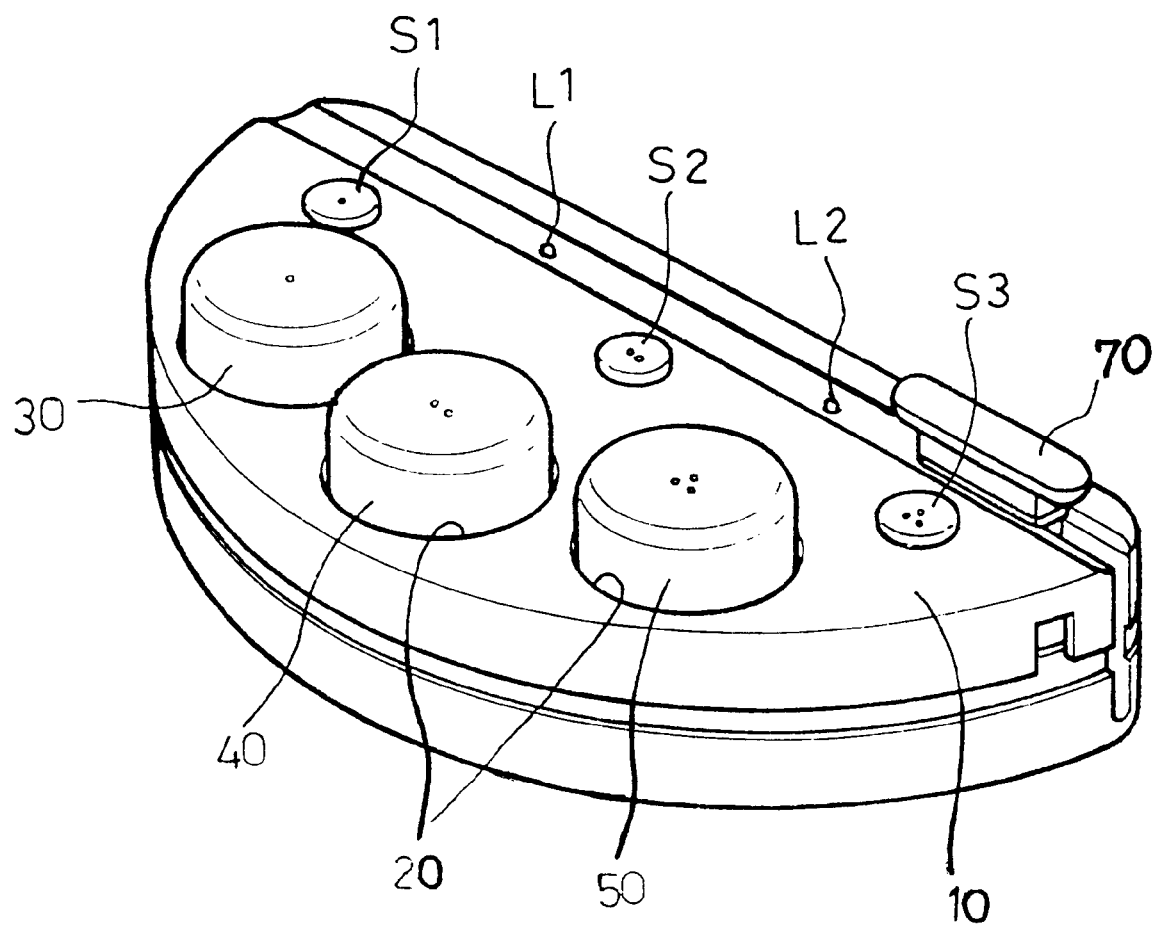
FIG. 1 is a schematic perspective view of an ion facial massage system in an assembled state, according to the present invention.
Figure 2:
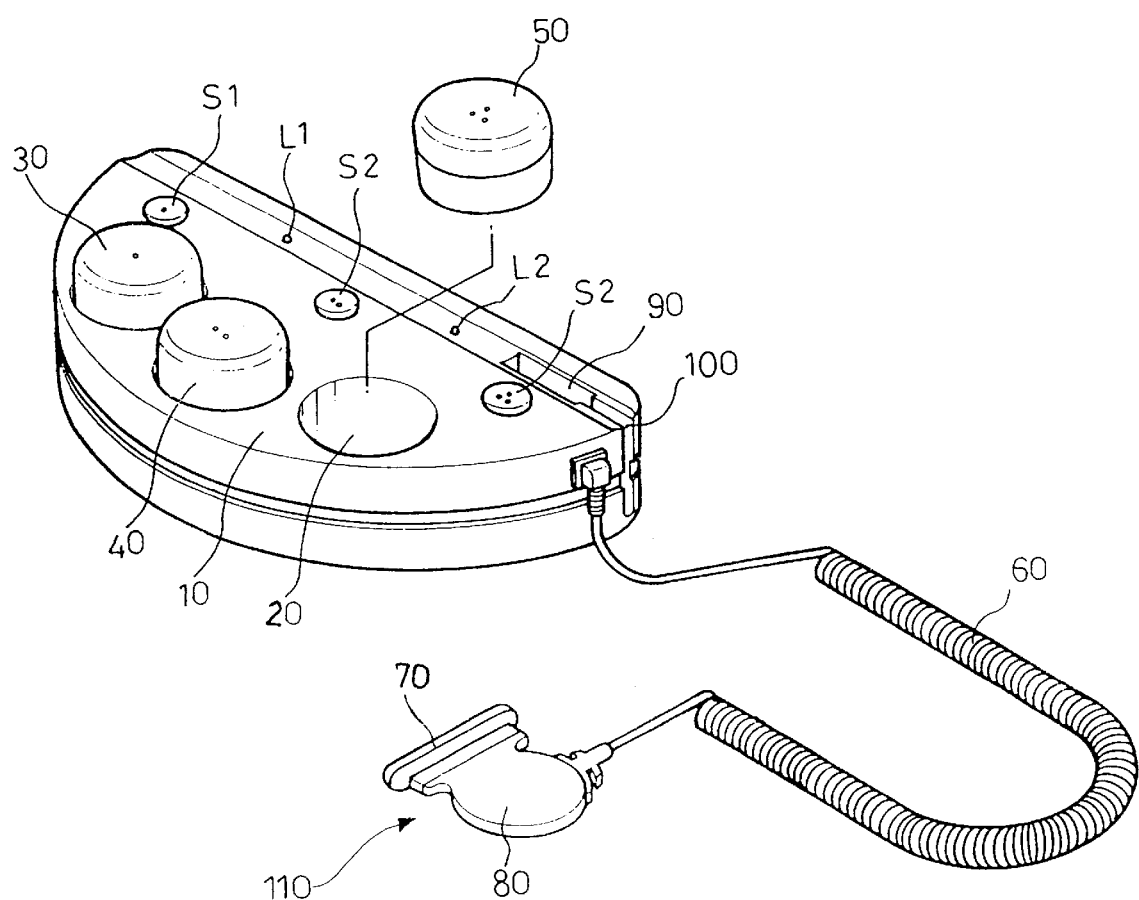
FIG. 2 is a schematic perspective view of the facial massage system of FIG. 1, which is in a disassembled state.

FIG. 1 shows an assembled ion facial massage system according to the present invention and FIG. 2 shows a perspective view of the ion facial massage system of FIG. 1 which is disassembled.

Referring to FIG. 1 and FIG. 2, on a top of a case 10 are formed three circular grooves 20 into which a first to a third cosmetic containers 30–50 are inserted and fixed. On bottom surfaces of the circular grooves 20 formed small openings (not shown) penetrating a bottom surface of the case 10 for users to insert their fingers or any other instrument and push the cosmetic containers 30–50 upwardly. Therefore, if it is necessary, for example, to substitute the cosmetic containers, it is possible to draw the cosmetic containers out of the grooves 20.

On the top of the case 10, a first switch S1, a second switch S2, and a third switch S3 are respectively installed to carry out a first stage, a second stage and a third stage of a massage procedure. Also, a battery lamp L1 and an ion lamp L2 are respectively provided on the top of the case 10 respectively to display a battery-consuming state and to display an ion-generation state.

A handle 80 is movably mounted at one side of the case 10 via a line 60 and connected to an ion effusion member 70. The case 10 is also formed with an inserting groove 90 at one side thereof so that the handle 80 may be detachably fitted into the groove 90.

Further, the case 10 has a battery case on its bottom surface thereof, which is not shown.

Figure 3:
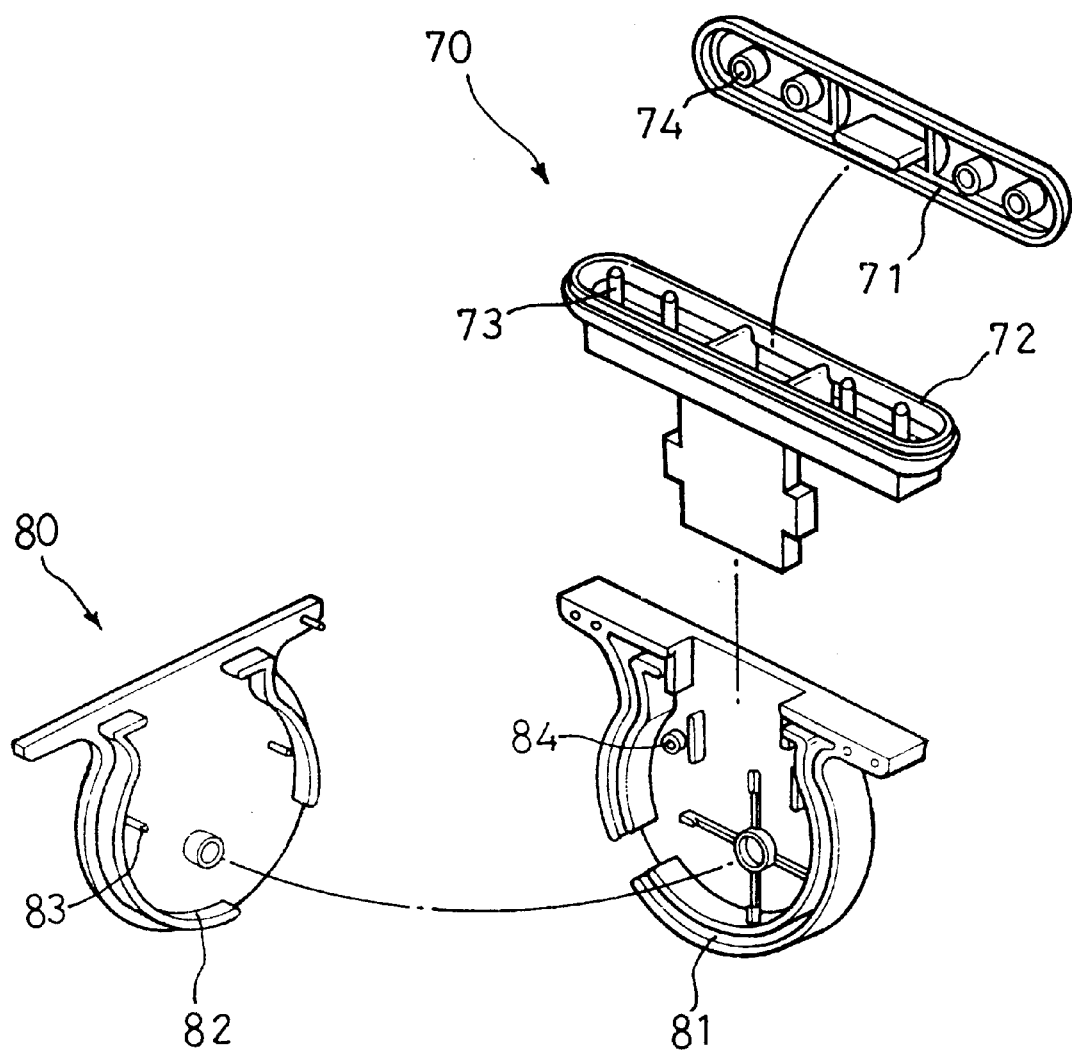
FIG. 3 is a schematic perspective view showing a handle and an ion effusion member of FIG. 1, which are in disassembled states.

FIG. 3 shows an ion-effusion part 10 including the handle 80 and the ion effusion member 70 in more detail, in which the handle 80 and the ion effusion member 70 are respectively shown in a disassembled state.

Referring to FIG. 3, the handle 80 may be divided into two pieces, of which one piece has peripheral groove parts 81 and protrusions 84 and the other one piece has peripheral protrusion part 82 and protrusions 83, so that the two pieces may be coupled by inserting the peripheral protrusions part 82 in the peripheral groove parts 81 and protrusions 83 in the protrusions 84.

The ion effusion member 70 may be divided into two pieces, of which one part has a plurality of protrusions 73 and peripheral protrusion parts 72, and the other one part has a plurality of grooves 74 and a peripheral groove part 71, so that the two part may be coupled by inserting the protrusions 73 in the grooves 74 and the peripheral protrusion parts 72 in the peripheral groove parts 71.

Figure 4:
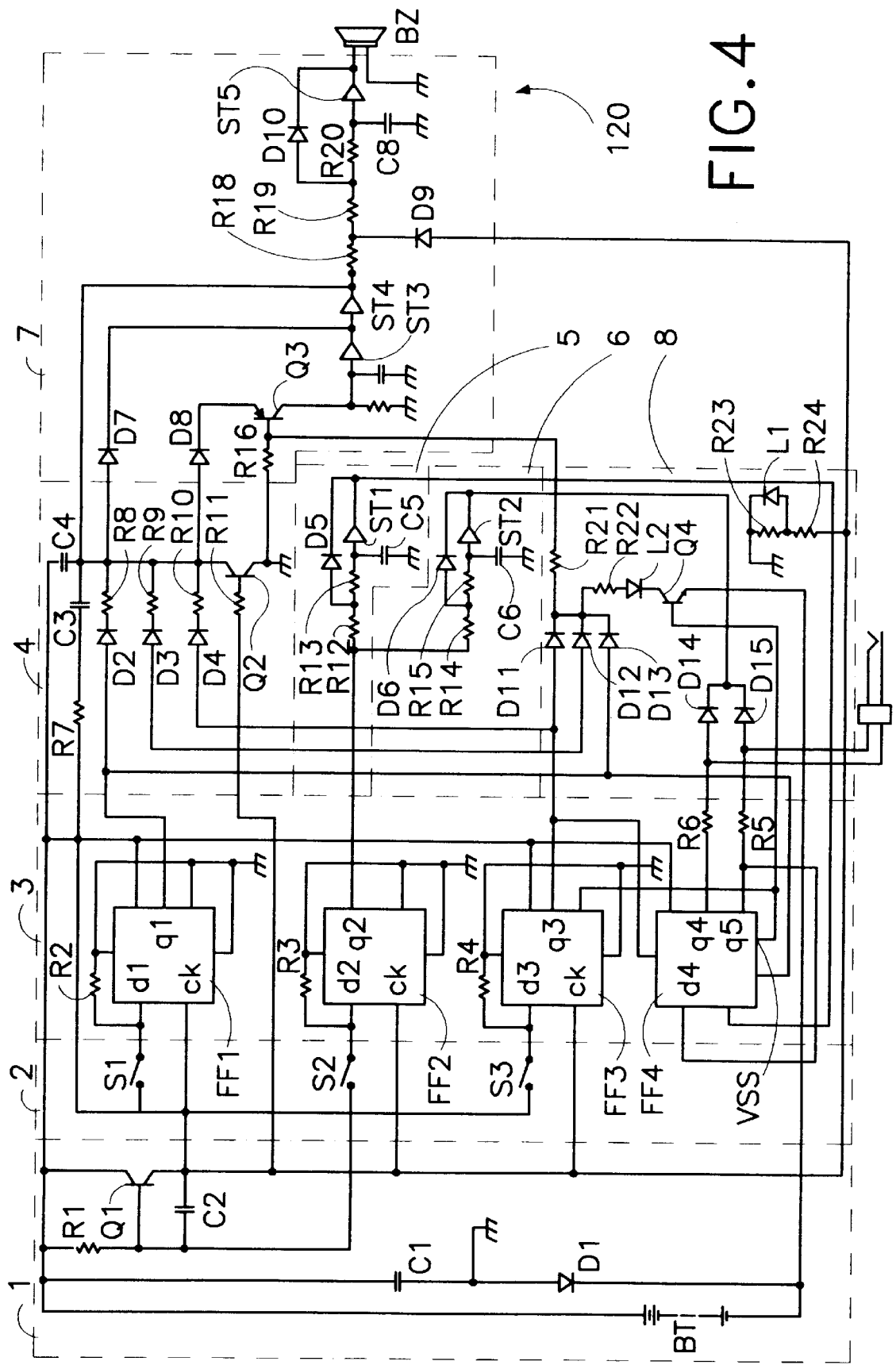
FIG. 4 is a schematic circuit diagram of an ion facial massage system according to the present invention.

FIG. 4 shows a circuit arrangement of an ion generation circuit part 120 of the ion facial massage system according to the present invention.

In FIG. 4, the ion generation circuit part 120 of the ion facial massage system includes a voltage supply 1 which has a resistor R1, condensers C1 and C2, a diode D1 and a transistor Q1, and supplies voltage BT to respective parts of the circuit, a switch part 2 which has switches SW1–SW3 to supply and/or cut off the voltage supply from the voltage supply 1, a flip-flop part 3 which has resistors R2–R6 and D-type flip-flops FF1–FF4, which operates selectively depending on the switching of the switching part 2, a buzzer setting part 4 which is connected to output terminals of the flip-flop part 3 and has resistors R7–R11, condensers C3 and C4, diodes D2–D4 and a transistor Q2 for setting an operating time period of a buzzer BZ, a first oscillating part 5 which has resistors R12 and R13, a condenser C5, a diode D5 and a schmit trigger ST1 for producing an oscillating signal to the buzzer BZ, a second oscillating part 6 which is connected to the first oscillating part 5 in parallel and has resistors R14 and R15, a condenser C6, a diode D6 and a schmit triggers ST2 to output an oscillating signal to the buzzer BZ, a third oscillating part 7 which includes resistors R16–R20, condensers C7 and C8, diodes D7–D10, schmit triggers ST3–ST5 and a transistor Q3 to output an oscillating signal to the buzzer BZ, and a display part 8 which has resistors R21–R24, diodes D11–D15, the battery lamp L1, the ion lamp L2, and a transistor Q4 for displaying ion-generatirng states and battery-consuming state by means of emitting diodes.

FIG. 5 shows respective wave forms of input/output signals of respective circuit parts for explaining operation of the ion facial massage system according to the present invention.

Now, massage operation of the ion facial massage system according to the present invention will be described in more detail.

The first to the third cosmetic containers respectively fulled with deep cleansing cream, toning and vitalizing gel, and hydro nutrition cream are respectively inserted into the circular inserting grooves 20 formed on the case 10 and fixed therein.

If a user pushes the first switch S1 to turn on the massage system after rubbing the deep cleansing cream in the first cosmetic container 30 into the skin, a buzzer sound is generated to inform of beginning of four minutes of a first stage, wherein the ion lamp L2 is lighted up to display that ions are generated.

Then, the user holds the handle 80 in such a manner that the ion effusion member 70 stands perpendicularly on the face, and rubs the face from a lower part to an upper part with the handle 80, keeping the ion effusion member 70 in contact with the face.

Since the transistor Q1 in the voltage supply part 1 is turned on during the first switch S1 is pressed, a high level signal b as shown in FIG. 5A is applied to the resistor R19 via the diode D9 of the third oscillating part 7, so that the buzzer BZ generates a sound by the schmit trigger ST5 and the ion lamp L2 of the display part 8 is lighted up by a high level signal a as shown in FIG. 5A.

At the same time, a pulse signal e as shown in FIG. 5A is applied to a data terminal d1 of the D-type flip-flop FF1 of the flip-flop part 3, of which set terminal and reset terminal are grounded, and a high level clock signal f as shown in FIG. 5A is applied to a clock terminal CK via the transistor Q1, so that the D-type flip-flop FF1 produces a high level output g.

Therefore, since the high level output g is applied to the condenser C4 via the diode D2 and the resistor R8 in the buzzer setting part 4, the condenser C4 begins to be charged to j as shown in FIG. 5A and, simultaneously, the signal g is applied to the transistor Q3 of the third oscillator 7 via the diode D13 and the resistor R21 of the display part 8 so that a base of the transistor Q3 is maintained high level and the transistor Q3 is turned off.

When an electric potential which is applied from the condenser C4 to an emitter of the transistor Q3 to charge the transistor Q3 via the diode D8 is higher than an electric potential which is applied from an output terminal q1 of the D-type flip-flop FF1 to the base of the transistor Q3 via the diode D13 and the resistor R21, the transistor Q3 is turned on and a potential of a collector of the transistor Q3 becomes high level.

The high level signal passes through the schmit triggers ST3 and ST4 and is applied as a high level signal to the clock terminal CK of the D-type flip-flop FF1 via the condenser C3, the resistor R7 and the condenser C2, so that the output signal g from the D-type flip-flop FF1 becomes low level and, simultaneously, the buzzer Bz generates a sound to inform the user of a lapse of the first operation time period by the oscillation of the third oscillating part 7. Until then, the user continuously performs the first stage of the massage.

The buzzer sound is continuously generated until the transistor Q3 is turned off as the electric potential charged to the condenser C4 by the resistor R8 is rapidly discharged to the transistor Q2 and a potential of an emitter of the transistor Q8 becomes lower than that of a base of the transistor Q8.

On the other hand, from the beginning of the generation of the buzzer sound by pressing the switch S1 to the second generation of the buzzer sound for informing the user of the lapse of the first operation time period, that is, while the high level signal g is output from the D-type flip-flop FF1, the high level signal g of the D-type flip-flop FF1 is applied to the collector of the transistor Q4 passing through the diode D13, the resistor R22, and the ion lamp L2 of the display part 8 in sequentially and, simultaneously, is applied to the reset terminal of the D-type flip-flop FF4.

In this case, since the set terminal of the D-type flip-flop FF4 is applied with a low level signal h as shown in FIG. 5A from the output terminal q3 of the D-type flip-flop FF3, the D-type flip-flop FF4 produces a low level signal n and a high level signal p regardless of the clock signal.

Furthermore, a low level signal i output from an output terminal q2 of the D-type flip-flop FF2 as shown in FIG. 5A is reversed into a high level signal l in the schmit trigger ST1 via the resistors R12 and R13 of the first oscillating part 5, and into a high level signal m in the schmit trigger ST2 via the resistors R14 and R15 of the second oscillating part 6. Therefore, the clock terminal CK of the D-type flip-flop FF4 is applied with the high level signal l and the D-type flip-flop FF4 produces the output signals n,p via the line 60.

Therefore, when the user rubs his face or other skin with the ion effusion member 70, current flows on the skin in the contact with the ion effusion member 70 so that the ions of the current, especially the negative ions having strong resolvent components, permeate the barrier zone and extract the effete materials and toxins in the outer and inrer skins to keep the skin clean and also to remove the effete materials and toxins out of the skin, thereby strengthening functions of capillary vessels and lymphatic glands.

While the outputs n,p from the D-type flip-flop FF4 are in contact with the skin via the resistors R5 and R6, the ion lamp L2 is lighted up since the transistor Q4 of the display part 8 is turned on by a bias voltage output from a terminal VSS of the D-type flip-flop FF4.

Now, a second stage of the massage is detailed in view of operation.

If the user pushes the second switch S2 to turn on the massage system after rubbing the toning and vitalizing gel in the second cosmetic container 40 into the skin, a buzzer sound is generated to inform the user of the beginning of eight minutes of the second operation time period, wherein the ion lamp L2 is lighted up to display that ions are generated.

Then, the user holds the handle 80 in such a manner that the ion effusion member 70 stands perpendicularly on the face, and rubs the face from a lower part to an upper part with the handle 80, keeping the ion effusion member 70 in contact with the face, wherein the user takes more gel if the rub is not smooth.

This second stage of the massage is for vitalizing deeper layers of skin through crossing movement of the positive and negative ions generated by the ion effusion member 70, thereby tightening the skin to be an elastic state by promoting metabolism.

After lapse of the eight minutes from the beginning of the second stage, the buzzer sound is generated and the ion lamp is turned off, thereby informing the user of the finish of the second stage of the massage. Then, the user cleans the face with warm wet towel and prepares the third stage.

Looking into the second stage in more detail, when the buzzer BZ generates a sound after a predetermined time period of the first stage as described hereinabove, the user cleans the skin with a warm wet towel and presses the second switch S2 to carry out the massage with the ion effusion member 70 after rubbing the gel in the second cosmetic container 40 into the skin.

Then, similar operations with those of the first stage are carried, so that the transistor Q1 in the voltage supply part 1 is turned on during the second switch S2 is pressed, a high level signal b of FIG. 5B is applied to the resistor R19 via the diode D9 of the third oscillating part 7. Therefore, the buzzer BZ generates a sound by the schmit trigger ST5 and the ion lamp L2 of the display part 8 is lighted up by a high level signal a of FIG. 5B, thereby indicating the second switch S2 has been pressed.

At the same time, since the high level output i as shown in FIG. 4B is applied from the output terminal q2 of the D-type flip-flop FF2 to the condenser C4 via the diode D2 and the resistor R8 in the buzzer setting part 4, the condenser C4 begins to be charged and the signal i is applied to the transistor Q3 of the third oscillator 7 vial the diode D12 and the resistor R21 of the display part 8 so that a potential at the base of the transistor Q3 is maintained high level and the transistor Q3 is turned off.

When an electric potential which is applied from the condenser C4 to the emitter of the transistor Q3 via a diode D8 to charge the transistor Q3 is higher than an electric potential which is applied from the output terminal q2 of the D-type flip-flop FF2 to the base of the transistor Q3 via the diode D12 and the resistor R21, the transistor Q3 is turned on and a potential of the collector of the transistor Q3 becomes high level.

The high level signal passes through the schmit triggers ST3 and ST4 and is applied as a high level signal f of FIG. 5B, to a clock terminal CK of the D-type flip-flop FF2 via the condenser C3 and the resistor R7, so that the output signal i from the D-type flip-flop FF2 becomes a low level signal and, simultaneously, the buzzer BZ generates a sound to inform the user of the lapse of the second operation time period by being oscillated by the third oscillating part 7. Until then, the user continuously performs the second stage of the massage.

The buzzer sound is continuously generated until the transistor Q3 is turned off as the electric potential of the condenser C4 is rapidly discharged to the transistor Q2 and a potential of the emitter of the transistor Q3 becomes lower than that Df the base of the transistor Q3.

On the other hand, from the beginning of the generation of the buzzer sound by pressing the switch S2 to the second generation of the buzzer sound for informing the user of the lapse of the second operation time period, that is, while the high level signal i is output from the D-type flip-flop FF2, the high level signal i of the D-type flip-flop FF1 is applied to the collector of the transistor Q4 passing through the diode D12, the resistor R22, and the ion lamp L2 of the display part 8 in sequentially.

Therefore, the clock terminal CK of the D-type flip-flop FF4 and cathodes of the diodes D14 and D15 in the display part 8 are respectively applied with high level signals l, m which have been reversed by the respective oscillating parts 5 and 6 via the resistors R12 and R14.

In this case, since the reset terminal of the D-type flip-flop FF4 is applied with a low level signal h, the D-type flip-flop FF4 produces signals n, p from its output terminals q4 and q5 according to signals input to the data terminal d4, in response to the signal l input to the clock terminal CK.

Wherein, since the clock terminal CR of the D-type flip-flop FF4 is applied with the high level signal l, the output terminals q4 and q5 of the D-type flip-flop FF4 generates positive ions (+) and negative ions (−) oppositely each other and, simultaneously, the oscillated output m of the second oscillating part 6 is applied to cathodes of the diodes D14 and D15.

Conclusionally, the output signals n,p from the output terminals q4, q5 of the D-type flip-flop FF4 and the oscillating signal m applied to the cathodes of the diode D14 and D15 are synthesized together, so that output signals s,t from the handle 80 have a predetermined waveform and their positives ions (+) and the negative ions (−) are alternate each other.

Therefore, differently from the first stage, since the synthetic signals s,t at the anodes of the diodes D14 and D15 are supplied to the handle 80 via the line 60, the positive and negative currents (+,−) are generated by the signals synthesized with the positive ions(+) and the negative ions(−) having a predetermined waveform and flows on the skin which is in contact therewith.

The positive and negative currents (+,−) flow alternately, so that skin functions such as cytotropism is strengthened, regeneration and fission of the basal cells are promoted, functions of aged capillary vessels and lymphatic glands are regenerated, the effete materials are removed and aging of skin is prevented, and nutrition components in the cosmetics may be absorbed deep into the inner skin.

In this case, the terminal VSS of the D-type flip-flop FF4 produces high level signals and low level signals repeatedly and the transistor Q3 of the display part 8 is repeatedly turned on and off, so that the ion lamp L2 becomes blinking.

Such a state is continued during the charging/discharging time period of the condenser C4 until the buzzer BZ generates a sound for informing the user of the finish of the second stage.

As the second stage is finished as above, the third stage of the massage procedure begins.

If the user pushes the third switch S3 to turn on the massage system after rubbing hydro nutrient cream in the third cosmetic container 50 into the skin smoothly preventing the cream from being absorbed into the skin, a buzzer sound is generated to inform the user of beginning of four minutes of the third stage, wherein the ion lamp L2 is lighted up to display that ions are generated.

Then, the user holds the handle 80 in such a manner that the ion effusion member 70 stands perpendicularly on the face, and rubs the face from a lower part to an upper part with the handle 80, keeping the ion effusion member 70 in contact with the face This third stage of the massage is to supply various high quality of nutrition components and collagen component deep into the inner skin beyond the barrier zone with the positive ions (+) which are generated by the ion effusion member 70, thereby making the skin dewy and glossy.

After lapse of the four minutes from the beginning of the third operating time period, the buzzer sound is generated and the ion lamp is turned off, thereby informing the user of the finish of the third stage of the massage.

That is, in the third stage, similar operations with those of the first stage are carried out, so that the transistor Q1 in the voltage supply part 1 is turned on during the third switch S3 is pressed, a high level signal a of FIG. 5C is applied to the resistor R19 via the diode D9 of the third oscillating part 7, thereby indicating the third switch S3 has been pressed.

At the same time, since a high level output has shown in FIG. 5C is applied from the output terminal q3 of the D-type flip-flop FF3 to the condenser C4 via the diode D4 and the resistor R10 in the buzzer setting part 4, the condenser C4 begins to be charged, and the signal h is applied to the transistor Q3 of the third oscillator 7 via the diode D11 and the resistor R21 of the display part 8, so that a potential at the base of the transistor Q3 is maintained high level and the transistor Q3 is turned off.

When an electric potential which is applied from the condenser C4 to the emitter of the transistor Q3 via the diode D8 to charge the transistor Q3 is higher than an electric potential which is applied from the output terminal q3 of the D-type flip-flop FF3 to the base of the transistor Q3 via the diode D11 and the resistor R21, the transistor Q3 is turned on and a collector potential of the transistor Q3 becomes high level.

The high level signal passes through the schmit triggers ST3 and ST4 and is applied as the high level signal f of FIG. 5B, to the clock terminal CK of the D-type flip-flop FF2 via the condenser C3, the resistor R7 and the condenser C2, so that the output signal h from the D-type flip-flop FF3 becomes low level and, simultaneously, the buzzer BZ generates a sound to inform the user of the lapse of the third stage time period by being oscillated by the third oscillating part 7. Until then, the user continuously performs the massage with the ion effusion member 70.

The buzzer sound is continuously generated until the transistor Q3 is turned off as the electric potential charged in the condenser C4 is rapidly discharged to the transistor Q2 and a potential of the emitter of the transistor Q3 becomes lower than that of the base of the transistor Q3.

On the other hand, from the beginning of the generation of the buzzer sound by pressing the switch S3 to the second generation of the buzzer sound for informing the user of the lapse of the third operation time period, that is, while the high level signal h is output from the output terminal q3 of the D-type flip-flop FF3, the high level signal h of the D-type flip-flop FF3 is applied to the collector of the transistor Q4 passing sequentially through the diodes D11, the resistor R22, and the ion lamp L2 of the display part 8 and, simultaneously, applied to the set terminal of the D-type flip-flop FF4.

At this time, since the set terminal of the D-type flip-flop FF4 is applied with the low level signal g, the output of the D-type flip-flop FF4 is a high level signal n and a low level signal p, regardless of the clock signals.

Furthermore, a low level signal i output from the output terminal q2 of the D-type flip-flop FF2 as shown in FIG. 5C is reversed into the high level signal l in the schmit trigger ST1 via the resistors R12 and R13 of the first oscillating part 5, and into the high level signal m in the schmit trigger ST2 via the resistors R14 and R15 of the second oscillating part 6. Therefore, the cathodes of the diodes D14 and D15 in the display part 8 are maintained high level and the clock terminal CK of the D-type flip-flop FF4 is applied with a high level signal l and the D-type flip-flop FF4 produces output signals n,p via the line 60.

Therefore, when the user rubs his face or other skin with the ion effusion member 70, current flows on the skin which is in contact with the ion effusion member 70 so that the positive ions (+) of the current makes the nutrition components of the cosmetics be absorbed deep into the inner skin, thereby strengthening the elasticity of the cellula tissue of the inner skin and the generation function of natural hydration factors, and promoting fission functions of new cells.

After the massage procedure is fully finished through the above described three stages, the handle 80 may be detachably fixed in the groove 90 formed in the side of the case by pushing it down into the groove 90, as shown in FIG. 1. Further, the line 60 of the handle 80 is fitted into a groove 100 which is integrally formed in the groove 90.

When the user desires to change the cosmetic containers 30–50, if the user pushes the bottoms of the cosmetic containers 30–50 through the openings formed on the bottom surface of the case 10, the containers may be easily detached from the case 10 and new containers may also be easily inserted into the grooves 20 of the case 10 by pushing then down into the grooves 20.

Further, the handle 80 is assembled with two pieces and the pieces are provided with protrusions, protruded peripheral parts, grooves and peripheral groove parts, so that cosmetics and moisture are prevented from soaking into the inside of the handle 80.

Furthermore, the ion effusion member 70 is assembled with two pieces and the pieces are provided with protrusions, a protruded peripheral part, grooves and a peripheral groove part, so that cosmetics and moisture are prevented from soaking into the inside of the ion effusion member 70.

EFFECT OF THE INVENTION

As described hereinabove, according to the ion facial massage system of the present invention, effete materials may be removed, and the nutritior components of the cosmetics and collagen may be absorbed deep into the inner skin beyond the barrier zone by means of positive and negative ions, thereby strengthening the elasticity of the cellula tissue in the inner skin and the generation function of natural hydration factors, and promoting fission functions of new cells.

Further, due to the compact and close assemble structure of the handle and the ion effusion member in the present ion facial massage system, mechanical troubles or electrical short may be prevented by protecting the insides thereof from the moisture and cosmetics as well as the handle and the ion effusion member are easy to disassemble or assemble in any necessary situations.

What is claimed is:

1. An ion facial massage system, comprising:

a case including a plurality of grooves formed on a top surface thereof for being inserted with cosmetic containers respectively, a plurality of switches provided at one side of said case for being pressed to carry out respective stages of massage, an ion lamp provided at one side of said case for displaying ion-generating states, and a battery lamp provided at one side of said case for displaying battery-consuming states;

ion-generating means incorporated in said case for electrically generating ions for the respective stages of massage when the switches on said case are selectively pressed; and ion-effusion means to be detachably fitted in an inserting groove formed on said case for effusing the electrically generated ions.

2. The system of claim 1, wherein said case includes a plurality of openings formed on a bottom surface thereof at corresponding positions to the grooves for inserting the cosmetic containers, so that the cosmetic containers may be detached from the grooves by pushing the cosmetic containers upwardly through the openings.

3. The system of claim 1, wherein said ion-generating means comprises:

a voltage supply part including a resistor (R1), condensers (C1, C2), a diode (D1) and a transistor (Q1) for supplying voltage to respective circuit parts;

a switch part including a plurality of switches (SW1–SW3) for supplying or cutting off the voltage from said voltage supply part;

a flip-flop part including resistors (R2–R6) and D-type flip-flops (FF1–FF4) which operate electively according to switching operation of said switch part;

a buzzer setting part being connected to output terminals of said flip-flop part and including resistors (R7–R11), condensers (D3, C4), diodes (D2–D4) and a transistor (Q2) for setting operating time of a buzzer;

a first oscillating part including resistors (R12, R13), a condenser (C5), a diode (D5) and a schmit trigger (ST1) for producing an oscillating output to said buzzer;

a second oscillating part being connected to said first oscillating part in parallel and including resistors (R14, R15), a condenser (C6), a diode (D6) and a schmit trigger (ST2) for producing an oscillating output to said buzzer;

a third oscillating part including resistors (R16–R20), condensers (C7, C8), diodes (D7–D10), schmit triggers (ST3–ST5), a transistor (Q3) for producing an oscillating output to said buzzer; and a display part including resistors (R21–R24), diodes (D11–D15), a battery lamp, an ion lamp, and a transistor (Q4) for displaying ion-generating states and battery-consuming states by means of light emitting diodes.

4. The system of claim 1, wherein said ion-effusing means comprises a handle and an ion-effusion member which respectively includes two pieces, each one piece having peripheral protrusion parts and protrusions and each of the other pieces having peripheral groove parts and grooves to be coupled together by inserting the peripheral protrusion parts and the protrusions in the peripheral groove parts and the grooves.

* * * * *